(12) United States Patent
Shugarman (10) Patent No.: US 10,130,351 B2
(45) Date of Patent: Nov. 20, 2018

(54) EYELID SPECULUM (71) Applicant: Shugarman Surgical Innovations, LLC, West Palm Beach, FL (US)

(72) Inventor: Richard G. Shugarman, West Palm Beach, FL (US)

(73) Assignee: Shugarman Surgical Innovations, LLC, West Palm Beach, FL (US)

( * ) Notice: Subject to any disclaimer, the term of this patent is extended or adjusted under 35 U.S.C. 154(b) by 152 days.

(21) Appl. No.: 15/235,186

(22) Filed: Aug. 12, 2016

(65) Prior Publication Data

US 2017/0042529 A1 Feb. 16, 2017

Related U.S. Application Data (60) Provisional application No. 62/204,752, filed on Aug. 13, 2015.

(51) Int. Cl.
*A61B 17/02* (2006.01)

(52) U.S. Cl.
CPC .......... *A61B 17/0231* (2013.01); *A61B 17/02* (2013.01)

(58) Field of Classification Search
CPC ............................ A61B 17/02; A61B 17/0231
See application file for complete search history.

(56) References Cited

U.S. PATENT DOCUMENTS

| 5,433,190 | A | 7/1995 | Sunalp |
| 6,083,155 | A | 7/2000 | Trese |
| 6,267,752 | B1 | 7/2001 | Svetliza |
| 6,440,065 | B1 | 8/2002 | Hered |
| D489,130 | S | 4/2004 | Sinding |
| D498,531 | S | 11/2004 | Sinding |
| D500,360 | S | 12/2004 | Sinding |
| D505,203 | S | 5/2005 | Sinding |
| 8,066,635 | B2 * | 11/2011 | Beck ........................ A61B 1/32 600/236 |
| 8,439,833 | B2 * | 5/2013 | Christensen ....... A61B 17/0231 600/236 |
| 8,678,593 | B2 * | 3/2014 | Abt ........................ A61B 3/125 351/212 |
| 8,936,550 | B2 | 1/2015 | Urano et al. |
| 9,144,516 | B2 | 9/2015 | Goncalves |

(Continued)

FOREIGN PATENT DOCUMENTS

| CN | 201098215 Y | 8/2008 |
| GB | 114051 | 3/1918 |

(Continued)

OTHER PUBLICATIONS

Intra Vitreal Injections Intra Vitreal Injection Assistant (In Vitria®), ttp://www.fciworldwide.com/index.php?I_idpa=67, 2 pages, Sep. 21, 2015, Copyright © 2012 FCI S.A.S., Paris France.

(Continued)

Primary Examiner — Larry E Waggle, Jr.
(74) Attorney, Agent, or Firm — McGarry Bair PC (57) ABSTRACT An eyelid speculum used to hold the eyelids of a patient's eye open during a medical procedure includes two retractors which are configured to engage the edge of a patient's eyelid and a central opening between the retractors which permits the medical practitioner to view the cornea of a patient's eye during a medical procedure. The eyelid speculum can be provided in a sterile medical kit.

20 Claims, 8 Drawing Sheets (56) References Cited

U.S. PATENT DOCUMENTS 9,795,504 B2 * 10/2017 Sayegh .................. A61F 9/007
2005/0288697 A1 * 12/2005 Tei ..................... A61B 17/3403
606/166

FOREIGN PATENT DOCUMENTS

| | | |
|---|---|---|
| GB | 116547 | 6/1918 |
| GB | 2382779 A | 11/2013 |
| JP | 2005512662 A | 5/2005 |
| JP | 2006320372 A | 11/2006 |
| JP | 2007151739 A | 6/2007 |
| JP | 4416695 B2 | 2/2010 |
| KR | 1020120118277 A | 10/2012 |
| WO | 2003053229 A2 | 7/2003 |
| WO | WO 03053229 A2 * | 7/2003 ............... A61B 1/32 |

OTHER PUBLICATIONS

InVitria Injection Assistant Now Available for Popular AMD Injections, published Mar. 31, 2015, 2 pages, accessed Sep. 21, 2015, Copyright © 2011 FCI Ophthalmics, Pembroke, Massachusetts.
Ki Yun Cho, International Search Report, dated Oct. 21, 2016, International Application Division of Korean Intellectual Property Office, Republic of Korea, 7 pages.

* cited by examiner

EYELID SPECULUM

CROSS-REFERENCE TO RELATED APPLICATION(S)

This application claims the benefit of U.S. Provisional Patent Application No. 62/204,752, filed Aug. 13, 2015, which is incorporated herein by reference in its entirety.

BACKGROUND

An eyelid speculum is a device used to hold a patient's eyelids open for a medical procedure, including ocular surgery, treatment, examination, or some other reason. Such medical procedures may be performed on both human and animal patients. Prior art speculum devices include retractors used to retract a patient's eyelids. This type of retractor speculum includes two moveable arms or blades, each of which engages one eyelid. Other speculums have been made from loops of wire the engage the eyelids.

BRIEF SUMMARY

The invention relates to an eyelid speculum. In one aspect, the invention relates to an eyelid speculum used to hold the eyelids of a patient's eye open during a medical procedure. The eyelid speculum can include a ring-shaped body, a pair of eyelid retractors which are configured to engage the edge of a patient's eyelids, and a central opening between the retractors which permits the medical practitioner to view the cornea of a patient's eye during a medical procedure. When applied to a patient's eye, the ring-shaped body fits on the conjunctiva and sclera of the patient's eye, with the posterior surface resting on the patient's eye and with the central opening exposing the cornea.

DESCRIPTION OF EMBODIMENTS OF THE INVENTION

The described embodiments of the present invention are directed to an eyelid speculum used to hold the eyelids open during a medical procedure. The eyelid speculum may be packaged in a sterile kit. As used herein, the term patient includes both human and animal patients of various ages and sizes. As used herein, the term medical procedure includes surgery, treatment, diagnosis, or examination of the patient's eye. As used herein, the term medical practitioner includes, but is not limited to, surgeons, nurses, and doctors, including at least ophthalmologists, and other medical professionals. It is also noted that one or more medical practitioners may be involved during the insertion and use of the eyelid speculum, and that the embodiments of any methods described herein may be performed by one or medical practitioners.

Figure 1:
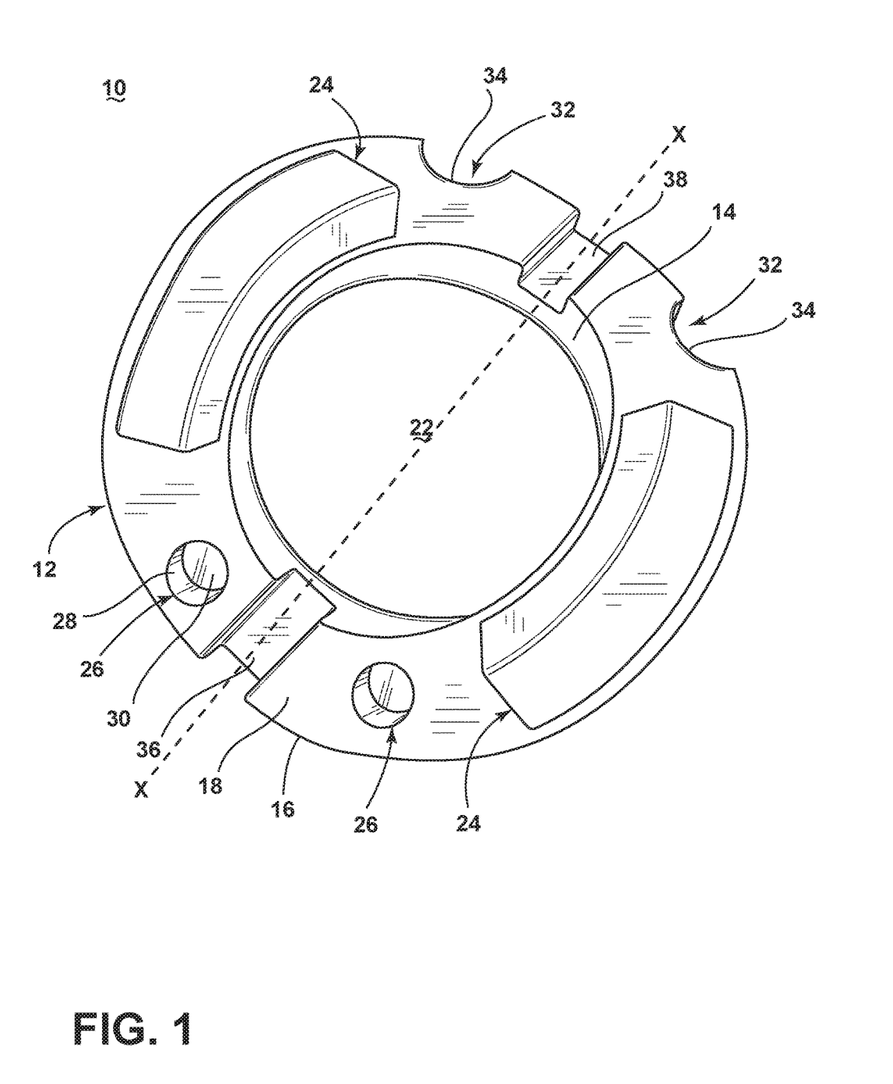
FIG. 1 is an anterior perspective view of an eyelid speculum according to one embodiment of the invention.
Figure 2:
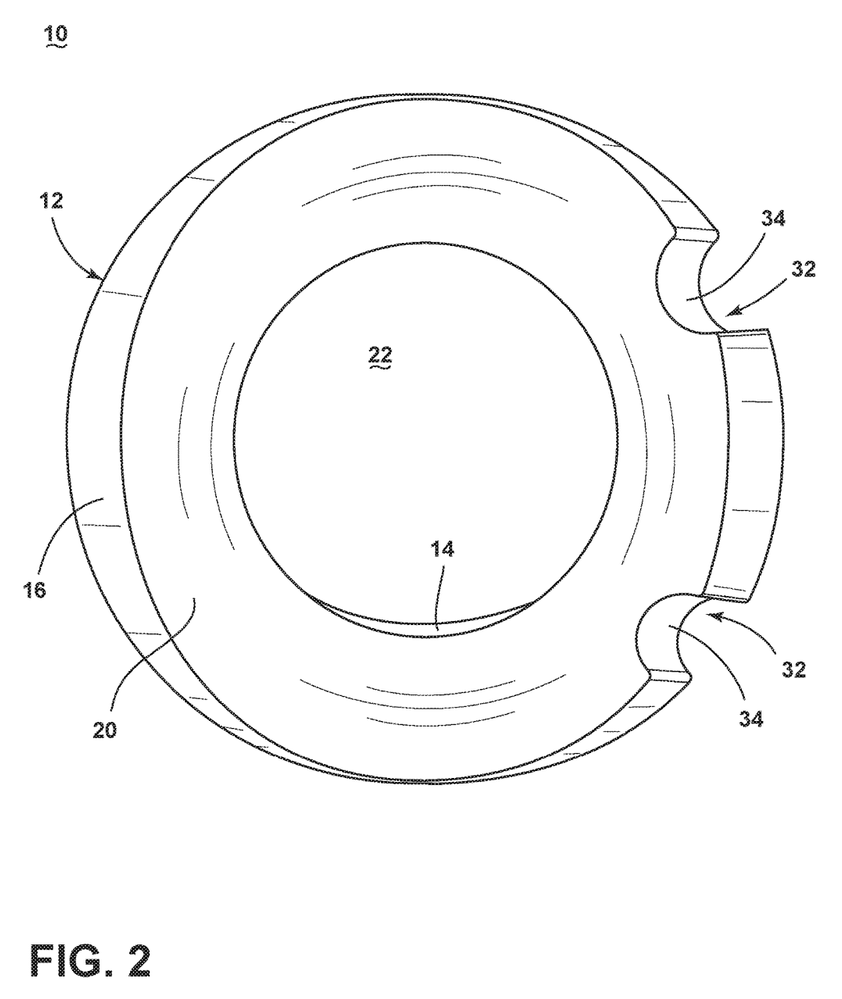
FIG. 2 is a posterior perspective view of the eyelid speculum from FIG. 1.

FIGS. 1-2 are anterior and posterior perspective views of an eyelid speculum 10 according to one embodiment of the invention. The eyelid speculum 10 includes a frame or body 12 that is insertable onto a patient's eye. The body 12 is ring-shaped, and includes an inner peripheral surface 14 and an outer peripheral surface 16 joining an anterior surface 18 and a posterior surface 20 of the body 12. A central opening 22 is defined by the inner peripheral surface 14 of the body 12.

The body 12 can include two retractors 24, which are configured to engage the edge of a patient's eyelid. The retractors 24 keep the eyelids open and the eyelashes out of the field of the medical procedure, reducing the possibility of infection and preventing the eyelids from blinking during the medical procedure. The retractors 24 can have a curvature adapted to the shape of the eyelid.

The central opening 22 permits the medical practitioner to view the cornea, anterior chamber, iris, and lens of a patient's eye during a medical procedure. The central opening 22 can be configured to fit around the cornea, which is not perfectly round. The shape of the central opening 22 can accordingly be circular, oblong, oval, elliptical, or other shapes which expose the entire cornea to view.

Optionally, the body 12 can be provided with one or more depressions 26 on the anterior surface 18, which can accommodate a cotton-tipped applicator or other depressor used for counter-pressure to steady the eye during the medical procedure and to aid in the insertion of a needle into the eye. The depressions 26 can be cup-shaped, with a side wall 28 extending from the anterior surface 18 to a bottom wall 30. In one example, gentle pressure directed horizontally, for example, applied against the side wall 28 in a direction generally toward the central opening 22, will steady the eye for the insertion of a needle, roughly 180 degrees from the depression, and not distort the eye or improperly elevate the intraocular pressure. When the eyelid speculum 10 is applied to the patient's eye, the depressions 26 can be oriented toward the medial canthus. In other embodiments, the depressions 26 can be oriented toward the lateral canthus in order to make injections on the opposite side of the eye.

Optionally, the body 12 can be provided with a set of recesses 32 in the outer peripheral surface 16 of the body 12. The recesses 32 are guides through which a needle may be inserted into the patient's eye for injection, aspiration, or release of fluid. When the speculum 10 is properly positioned in the eye, the recesses 32 expose a portion of the conjunctiva and sclera, and are configured to be located where the medical practitioner needs to insert a needle. The recesses 32 can be defined by an incurved section 34 of the outer peripheral surface 16. The recesses 32 can have a known diameter, which the medical practitioner can use as a marker or guideline for determining where to insert a needle. The recesses 32 allow the eyelid speculum 10 to be used in patients with smaller eyes, such as children, by providing the medical practitioner with a way of measuring distance for needle injections.

When the eyelid speculum 10 is applied to the patient's eye, the recesses 32 can be oriented toward the lateral canthus. In other embodiments, the recesses 32 can be oriented toward the medial canthus in order to make injections on the opposite side of the eye. The depressions 26 can be located generally 180 degrees from the recesses 32 in order to provide appropriate counter-pressure during an injection or aspiration.

Optionally, the body 12 can be provided with grooves 36, 38 connecting to the central opening 22 for anterior chamber paracentesis, aspiration, and/or injection. The grooves direct the needle horizontally, parallel to the iris plane, and steady the needle to reduce movement or "wiggle", and also make the injection perpendicular to the limbus. A medial groove 36 between the depressions 26 extends as a cavity in the anterior surface 18 between the inner and outer peripheral surfaces 14, 16. A lateral groove 38 between the recesses 32 extends as a cavity in the anterior surface 18 between the inner and outer peripheral surfaces 14, 16. When the eyelid speculum 10 is applied to the patient's eye, the medial groove 36 can be oriented toward the medial canthus and the lateral groove 38 can be oriented toward the lateral canthus.

Figure 3:
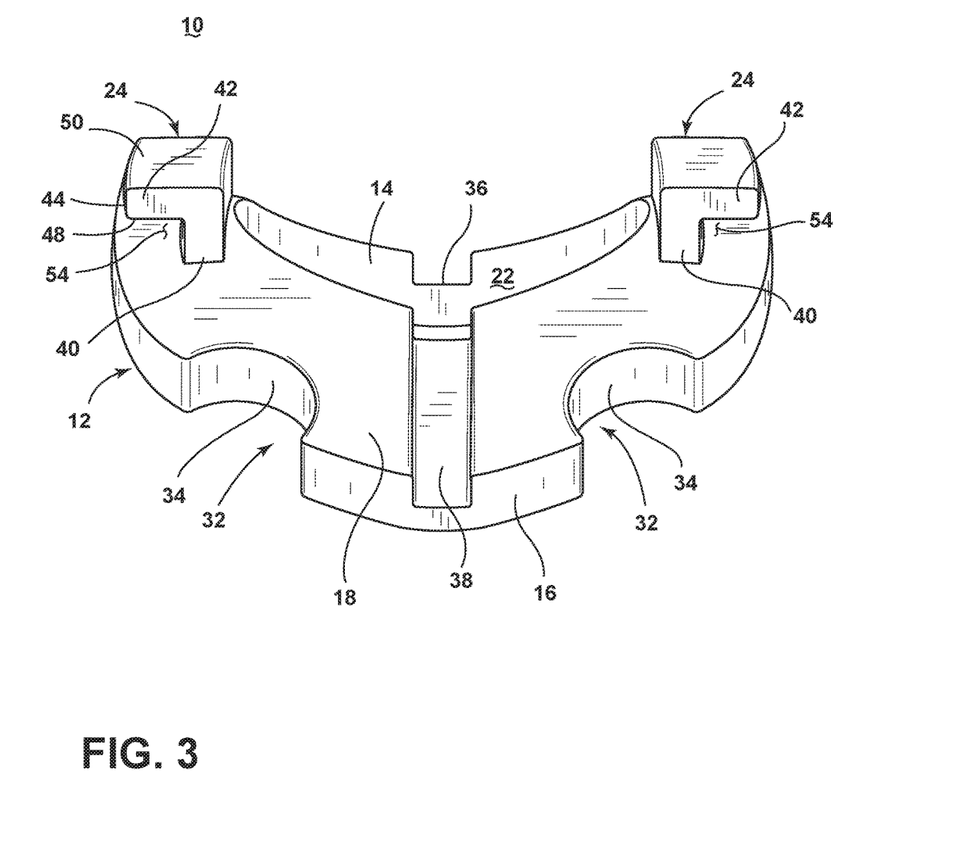
FIG. 3 is a side view of the eyelid speculum from FIG. 1.

FIG. 3 is a side view of the eyelid speculum 10 from FIG. 1. The retractors 24 are hooked-shaped, with an elongated support 40 and an elongated flange 42 extending from the support 40. The support 40 of the retractor 24 extends transversely across the anterior surface 18, and projects generally normally from the anterior surface 18 between the inner and outer peripheral surfaces 14, 16. The flange 42 of the retractor 24 extends from the support 40 to a hook end 44 facing toward the outer peripheral surface 16. The hook end 44 may be curved to comfortably fit a patient's eyelid, and may have a curvature similar to that of the outer peripheral surface 16.

The inner surfaces of the support 40 and flange 42 define an inner surface 48 of the retractor 24, which also has an obverse outer surface 50. The inner surface 48, along with the anterior surface 18, defines a pocket 54 which receive portions of the patient's eyelids.

When the eyelid speculum 10 is positioned in the patient's eye, the retractors 24 exert a force to hold the eyelids open. The retractors 24 can be configured to exert a predetermined amount of force, and the amount of force exerted by the retractors 24 against the eyelids when properly positioned can be configured according to the patient, such as whether the patient is an adult, child, or infant. The force exerted may be adjusted in other embodiments to accommodate the requirements of a specific category of patient.

The retractors 24 can be substantially identical to each other. Alternatively, the retractors 24 can be configured with respect to the anatomy of the superior and inferior eyelids, and may therefore differ in configuration.

The eyelid speculum 10 shown in FIGS. 1-3 is configured to be used on either the right or left eye of the patient. An imaginary axis X can be drawn through the speculum 10 to divide the speculum into generally identical superior and inferior halves which are mirror images of each other. One retractor 24 is provided on each half for retracting the eyelids, as well as one depression 26 and one recess 32. The grooves 36, 38 may run though the axis X.

Figure 4:
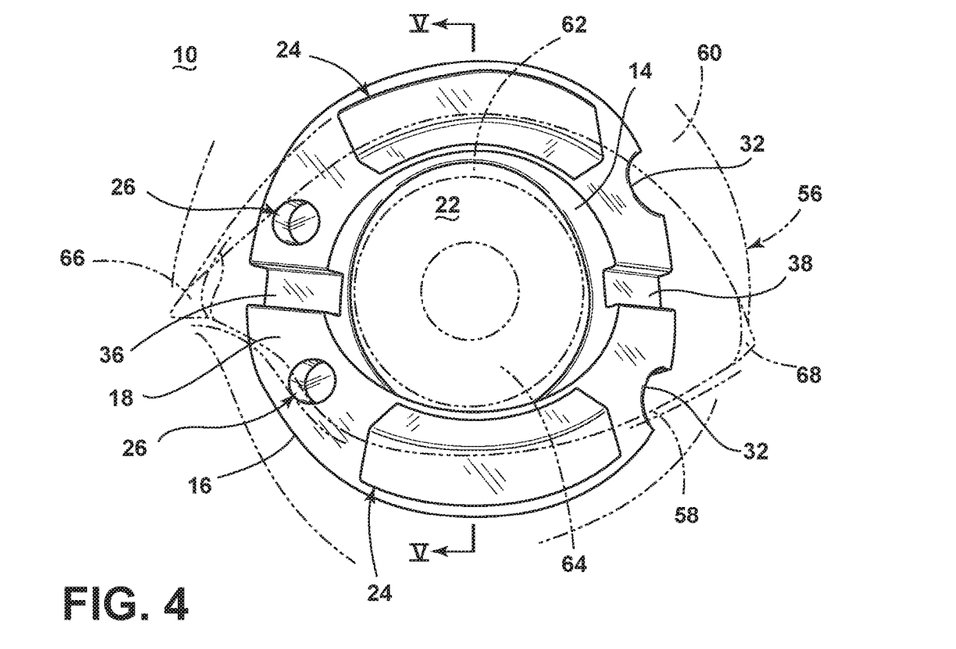
FIGS. 4 and 5 are illustrations showing the eyelids of a patient's eye being retracted by the eyelid speculum from FIG. 1.
Figure 5:
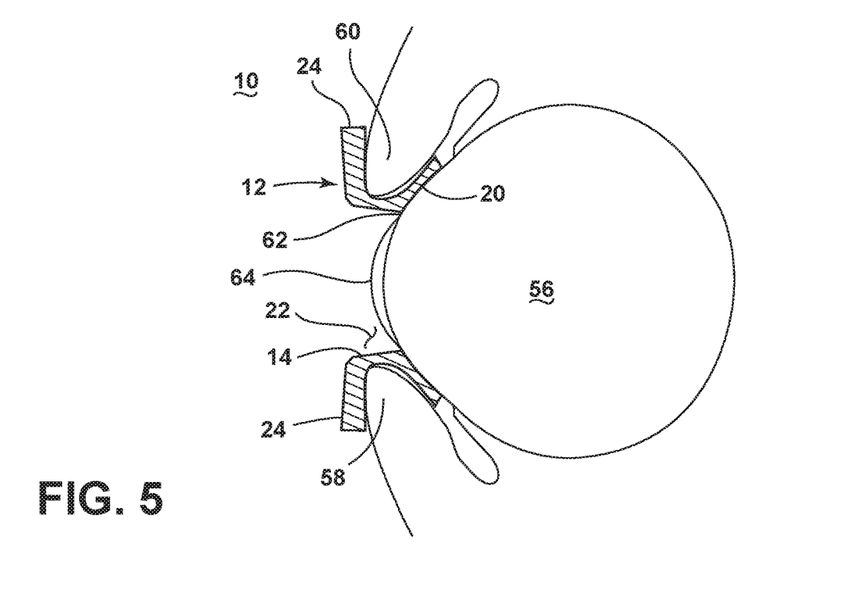

FIGS. 4 and 5 are illustrations showing the eyelids of a patient's eye 56 being retracted by the eyelid speculum 10 from FIG. 1. The patient can be in a supine or seated position while the eyelid speculum 10 is inserted, and during the subsequent medical procedure. Prior to insertion of the eyelid speculum 10, the medical practitioner can apply a topical anesthetic to the patient's eye, and prep the eyelids and lashes by cleaning the skin and eyelashes, and applying an antiseptic.

To insert the eyelid speculum 10 according to one embodiment of an insertion method, the patient opens their eye 56 wide and looks up. With the body 12 held at an angle, the medical practitioner slips the lower retractor 24 onto the inferior eyelid 58, pivots the body 12 up and toward the eye 56, and hooks the upper retractor 24 onto the superior eyelid 60. The eyelid speculum 10 can be removed in a similar manner. In another embodiment, the eyelid speculum can be inserted or removed like a contact lens.

When in place, the body 12 fits on the sclera 62 of the eye 56, which in this location is covered by conjunctiva, with the central opening 22 exposing the cornea 64. The depressions 26 and medial groove 36 can be positioned adjacent to the medial canthus 66, and the recesses 32 and lateral groove 38 can be positioned adjacent to the lateral canthus 68. The posterior surface 20 of the body 12 rests on the eye 56, similar to a contact lens.

With the eyelid speculum 10 positioned as shown in FIGS. 4 and 5, the medical practitioner may work on the iris or pupil of the cornea 64 through the central opening 22 while the eyelids 58, 60 are held in a retracted position by the retractors 24. Additionally, the medical practitioner may apply counter-pressure via the depressions 26 or inject a material via the grooves 36, 38.

Some specific examples of medical procedures during which the eyelid speculum 10 may be used include, but is not limited to, injection or withdrawal of material from the eye. For example, the eyelid speculum can be used to inject material, such as medicines or treatments including but not limited to, antibiotics, steroids, and anti-vascular endothelial growth factors (anti-VEGFs), into the vitreous or anterior chamber of the patient's eye. In another example, the eyelid speculum 10 can be used to withdraw intraocular fluids for diagnostic or therapeutic purposes.

The body 12 can be configured to fit the curvature of the sclera 62, which in this location is covered by conjunctiva. A radius of curvature that is significantly smaller than that of the sclera 62, i.e. a steeper curve, on the posterior surface 20 may make the speculum 10 difficult to remove as the body 12 may suction to the sclera 62. A radius of curvature that is significantly greater than that of the sclera 62, i.e. a shallower curve, on the posterior surface 20, may allow the speculum 10 to rock or move around during a medical procedure. In one example of an eyelid speculum 10 suitable for an adult human eye, the radius of curvature for the posterior surface 20 can be approximately 12 mm. Both the anterior and posterior surfaces 18, 20 of the speculum 10 may be curved. However the radius of curvature for the anterior surface 18 may be the same or different than that of the posterior surface 20.

The thickness of the body 12, defined as the distance between the anterior and posterior surfaces 18, 20, may be constant across the entire body 12, or may have sections of varying thickness. For example, the outer edges of the body 12 defined by the outer peripheral surface 16 may be thinner than the portion of the body 12 closer to the inner peripheral surface 14.

In one embodiment in which the eyelid speculum 10 is configured for use in an adult human patient, the body 12 can have an outer diameter of approximately 19.5 mm and a width, between the inner and outer peripheral surfaces 14, 16, of approximately 4 mm. The thickness of the body 12 can be up to 2 mm. Further, the central opening 22 can have a diameter of approximately 11-12 mm in diameter, and preferably approximately 11.5 mm or the average horizontal diameter of an adult human cornea. The depressions 26 can be approximately 1-1.5 mm deep and have a diameter of approximately 3.5 mm. The recesses 32 can be approximately 1 mm across, defining a radius of approximately 0.5 mm. The grooves 36, 38 can be approximately 1 mm deep and have a width of approximately 1.25 mm; like the body 12, the grooves 36, 38 can have a length of approximately 4 mm. The retractors 24 can be approximately 8 mm wide, when measured along the hook end 44, and may protrude a total of 4-6 mm from the anterior surface 18 of the body 12.

Features of the eyelid speculum 10 can be used as landmarks for making injections and/or aspirations. It is accepted practice to make vitreous injections and aspirations 3 to 4 mm from the limbus, the anatomical junction of the cornea and sclera. This permits the needle to enter into the pars plana, avoiding the lens and retina. Using the eyelid speculum 10, landmarks such as the outer peripheral surface 16 and the needle guide recesses 32 can be used to judge where to make a needle insertion, without requiring the use of a separate measuring instrument such as a sterile ruler or caliper.

For example, taking an eyelid speculum 10 having the dimensions described above, since the central opening 22 of the speculum 10 is preferably 11.5 mm, the average horizontal diameter of the cornea, and the width of the body 12 ring is preferably 4 mm, fine needle placement adjacent to the outer peripheral surface 16 will automatically enter the appropriate site, 4 mm from the limbus, eliminating the need for a separate sterile ruler or caliper. In another example, as the indentation of the two needle guide recesses 32 is preferably 1 mm at its deepest, i.e. 1 mm in from the outer peripheral surface 16, a medical practitioner can choose to inject at 3 or 3.5 mm from the limbus when appropriate as well, again, without using a second measuring instrument. In order to make such injections and/or aspirations even easier, indicia can be provided on the eyelid speculum to indicate these landmarks, such as by indicating the 3 and 3.5 mm measurements around the needle guide recesses 32 or the 4 mm measurement at the outer peripheral surface 16.

When a ruler is used during vitreous injections and aspirations, a third instrument in the form of a sterile marker must also be used to stain the proposed injection site. Likewise, caliper marks fade quickly and are best used in conjunction with a sterile marking pen. This adds expense and time to the procedure, as well as an additional source of contamination and possible infection. Even the finest tips available on these pens enlarge and blur, creating room for error as to the placement of the needle. A single instrument such as the eyelid speculum 10 can make the injection site more consistent and accurate than current alternatives, and can be used by the medical practitioner without an assistant to hand him/her the ruler, caliper, and/or marker.

The eyelid speculum 10 can be made in a variety of materials standard for ocular medical procedures, including, but not limited to, titanium, stainless steel, and polymethylmethacrylate (PMMA). Using titanium or stainless steel, the eyelid speculum 10 can be easily sterilized in autoclaves commonly found in medical offices, hospitals, or surgical centers, such that the eyelid speculum 10 can be used more than once.

Using PMMA, the eyelid speculum 10 can be pre-sterilized and disposed of after a single use. Other medical grade polymers can be used for disposable speculums as well. The PMMA version of the eyelid speculum 10 has a further advantage or giving the medical practitioner a view of the conjunctiva and sclera beneath the eyelid speculum 10 because PMMA can be transparent or clear. The eyelid speculum 10 made from PMMA or other polymeric material standard for ocular medical procedures can further be integrally molded in one piece.

It is noted that the retractors 24 may be more rigid than the body 12 through the selection of different materials for the retractors 24 and the rest of the body 12. This permits the body 12 to conform to the shape of the eyeball, without permanent deformation, while the retractors 24 are still robust enough to retract and hold the eyelids apart.

The eyelid speculum 10 made from PMMA or other material standard for ocular medical procedures can be packaged in separate or combined sterile packaging to provide a single-use, sterile kit for a medical procedure. In addition to the eyelid speculum, the kit can include a syringe, sterile cotton, antiseptic, a cotton-tipped applicator or other depressor, or any combination thereof. The items of the kit can be packaged in a sterilized condition. The kit can be intended for disposal after a single use. Other items such as disposable gloves, a face mask, sterile drapes, and instructions for using the kit, can also optionally be included. In one example, the instructions can be provided as one or more sheets of instructions inside the kit or instructions provided on a box or packaging for the kit.

Figure 6:
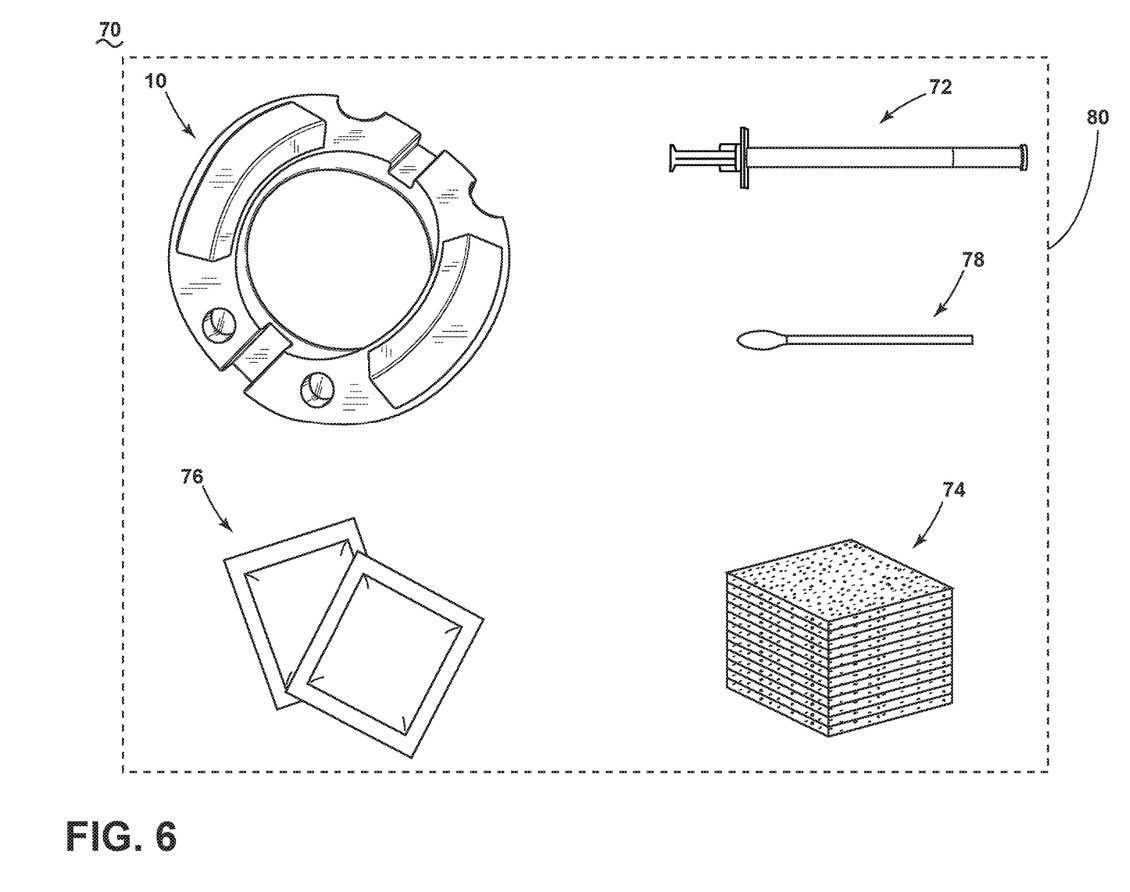
FIG. 6 is a schematic view of a sterile kit including the eyelid speculum from FIG. 1 according to another embodiment of the invention.

FIG. 6 shows one example of a sterile medical kit 70 according to one embodiment of the invention. The kit 70 can include, in addition to the eyelid speculum 10 described above or any other embodiments of an eyelid speculum disclosed herein, a syringe 72, sterile cotton 74, antiseptic 76 in the form of alcohol swabs or pads, at least one cotton-tipped applicator 78 or other depressor, or any combination thereof. The items of the kit 70 can be packaged in a sterilized condition in a sealed package 80 that is easily openable by a medical practitioner. Other items such as disposable gloves, a face mask, sterile drapes, and instructions for using the kit (not shown), can also optionally be included in the kit 70. The kit 70 can be intended for disposal after a single use. It is noted that the items of the kit 70 shown in FIG. 6 are not necessary drawn to scale relative to each other.

Figure 7:
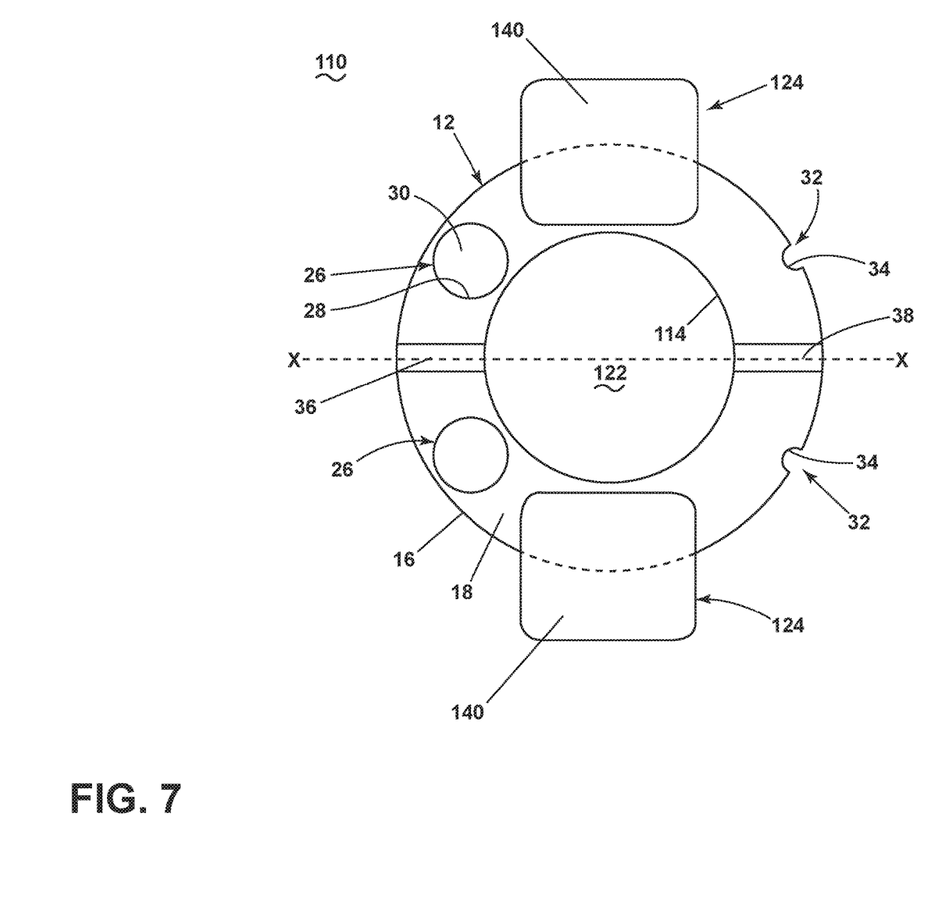
FIG. 7 is an anterior view of an eyelid speculum according to another embodiment of the invention.

FIG. 7 is an anterior view of an eyelid speculum 110 according to another embodiment of the invention. The eyelid speculum 110 is substantially similar to the eyelid speculum 10 of FIG. 1, and like elements are shown with like reference numbers. The eyelid speculum 110 can be substantially similar to the eyelid speculum 10 described above, including the exemplary dimensions and materials described above, save for the configuration of eyelid retractors 124, which are configured to engage the edge of a patient's eyelid, and some contouring of the body 12.

Figure 8:
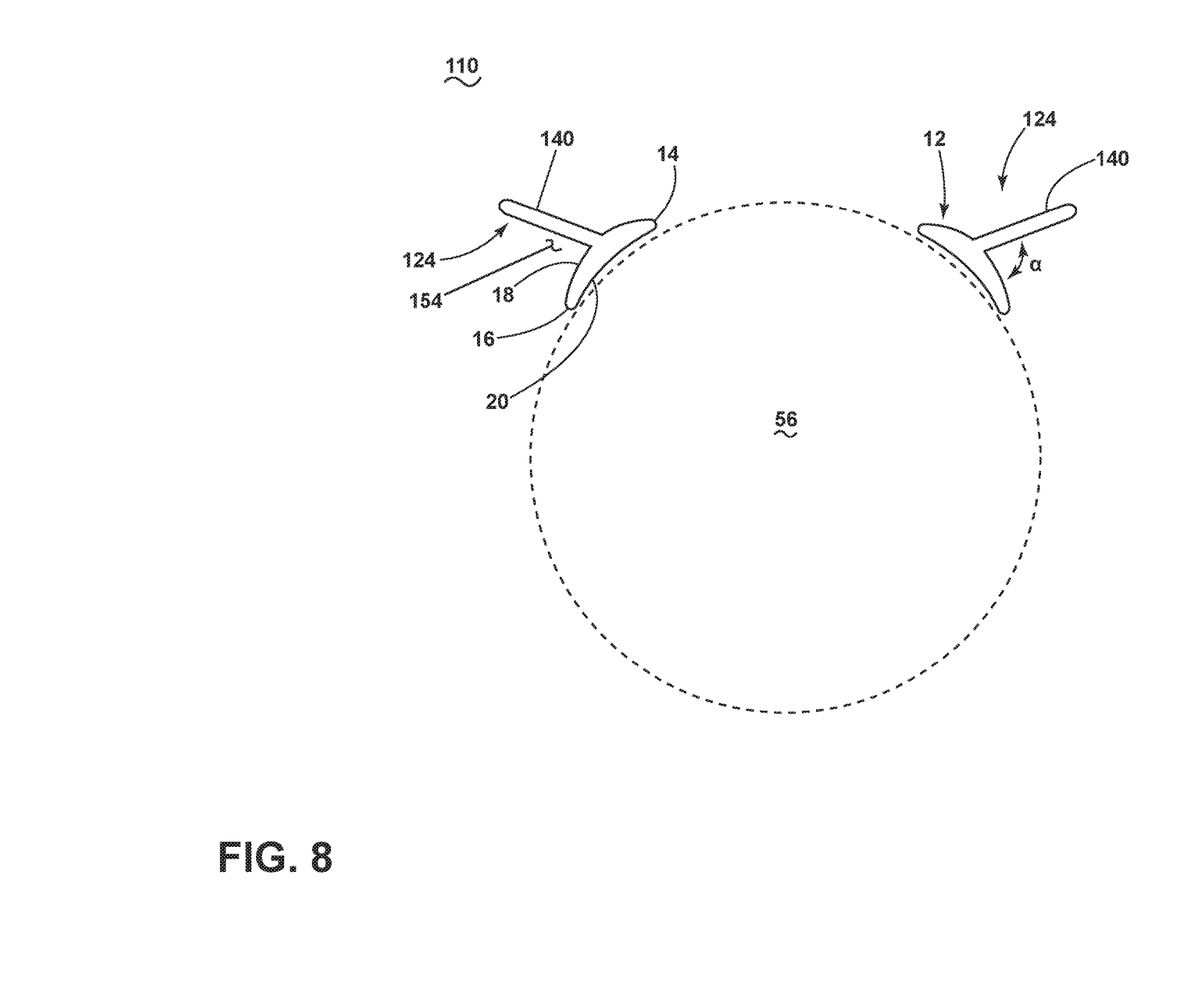
FIG. 8 is an illustration of the eyelid speculum from FIG. 7 on a patient's eye.

FIG. 8 is an illustration of the eyelid speculum 110 from FIG. 7 on a patient's eye 56. Like the first embodiment, the retractors 124 keep the eyelids open and the eyelashes out of the field of the medical procedure, reducing the possibility of infection and preventing the eyelids from blinking during the medical procedure. However, instead of being hook-shaped, the retractors 124 comprise a single elongated support 140 that extends at an angle α from the anterior surface 18 to form a V-shaped pocket 154 along with the anterior surface 18 for receiving a patient's eyelid. The support 140 extends transversely across the anterior surface 18, and projects generally normally from the anterior surface 18 between the inner and outer peripheral surfaces 14, 16.

The angle α at which the supports 140 extend away from the anterior surface 18 is preferably less than 90 degrees, or more preferably be between 30 and 60 degrees, or, as shown herein, may be 45 degrees. Also, while shown here as extending substantially straight in the transverse direction across the anterior surface 18, the supports 140 may be curved to comfortably fit a patient's eyelid, and may have a curvature similar to that of the inner peripheral surface 14 or the outer peripheral surface 16, or can have a curvature adapted to the shape of the eyelid.

In one embodiment in which the eyelid speculum 110 is configured for use in an adult human patient, the retractors 124 can be approximately 8 mm wide, when measured transversely across the anterior surface 18 (FIG. 7), approximately 1.5 mm thick, and may protrude a total of 4-6 mm, and more preferably 5 mm, from the anterior surface 18 of the body 12.

When the eyelid speculum 110 is positioned in the patient's eye 56, the retractors 124 exert a force to hold the eyelids open. The retractors 124 can be configured to exert a predetermined amount of force, and the amount of force exerted by the retractors 24 against the eyelids when properly positioned can be configured according to the patient, such as whether the patient is an adult, child, or infant. The force exerted may be adjusted in other embodiments to accommodate the requirements of a specific category of patient.

The retractors 124 can be substantially identical to each other. Alternatively, the retractors 124 can be configured with respect to the anatomy of the superior and inferior eyelids, and may therefore differ in configuration.

Further, as shown, the body 12 can be contoured for comfort, including having rounded edges at the inner and outer peripheral surfaces 14, 16. Furthermore, the thickness of the body 12, defined as the distance between the anterior and posterior surfaces 18, 20, may vary. For example, the edges of the body 12 defined at the inner and outer peripheral surfaces 14, 16 may be thinner than a central portion of the body 12 between the inner and outer peripheral surfaces 14, 16.

Figure 9:
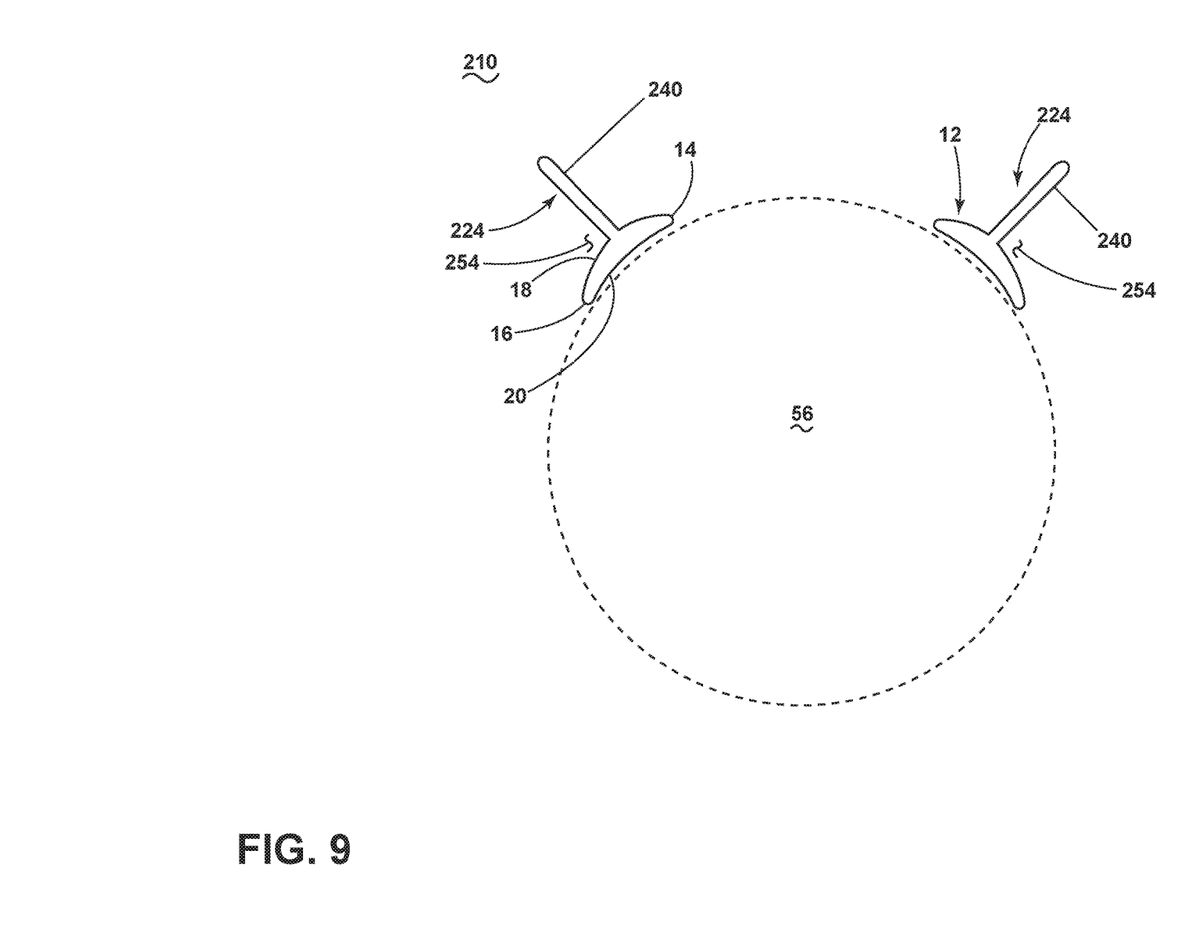
FIG. 9 is an illustration of an eyelid speculum according to another embodiment of the invention on a patient's eye.

FIG. 9 is an illustration of an eyelid speculum 210 according to another embodiment of the invention on a patient's eye 56. The eyelid speculum 210 is substantially similar to the eyelid speculum 210 of FIG. 7-8, and like elements are shown with like reference numbers. The eyelid speculum 210 can be substantially similar to the eyelid speculum 110 described above, including the exemplary dimensions and materials described above, save for the configuration of eyelid retractors 224. In the illustrated embodiment, the retractors 224 comprise supports 240 which extend normally from the anterior surface 18 to form an approximately 90-degree-sized pocket 254 along with the anterior surface 18 for receiving a patient's eyelid.

The various embodiments of systems, methods, and other devices related to the invention disclosed herein provide an improved eyelid speculum for holding the eyelids of a patient's eye open during a medical procedure. One advantage that may be realized in the practice of some embodiments of the described systems is that the eyelid speculum 10 is a one-piece assembly with no moving parts that is lightweight and comfortable for the patient, and is easily inserted by a medical practitioner. The patient can be either supine or seated when the eyelid speculum 10 is inserted, and during its use.

Another advantage that may be realized in the practice of some embodiments of the described systems is that the eyelid speculum 10 can permit a single medical practitioner to complete a medical procedure. For example, a surgeon can complete a medical procedure on a patient without the aid of a nurse or other assistant. The simple configuration allows the surgeon to readily apply the eyelid speculum 10 to the patient's eye, perform the medical procedure, and remove the eyelid speculum 10.

Yet another advantage that may be realized in the practice of some embodiments of the described systems is that the eyelid speculum 10 is designed to make injections and aspirations safe and accurate. The recesses 32 act as guides through which a needle may be inserted into the patient's eye, and the medical practitioner can use the recesses as a marker or guideline for determining where to insert a needle.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An eyelid speculum for holding eyelids of a patient's eye open during a medical procedure, comprising:
   a ring-shaped body insertable onto a patient's eye and including an inner peripheral surface, an outer peripheral surface, an anterior surface, and a posterior surface;
   a pair of eyelid retractors provided on the ring-shaped body;
   a central opening defined by the inner peripheral surface of the ring-shaped body, between the pair of eyelid retractors, which is sized to permit a view of a cornea of the patient's eye during the medical procedure;
   multiple depressions on the anterior surface of the ring-shaped body, separate from the pair of eyelid retractors; and
   multiple needle guide recesses in the outer peripheral surface of the ring-shaped body;
   wherein, when applied to the patient's eye, the ring-shaped body fits on a conjunctiva and sclera of the patient's eye, with the posterior surface resting on the patient's eye and with the central opening exposing the cornea; and
   wherein the multiple depressions are located generally 180 degrees from the needle guide recesses.

2. The eyelid speculum of claim 1, wherein the eyelid speculum defines an axis of symmetry that divides the eyelid speculum into generally identical superior and inferior halves, wherein one retractor is provided on the superior half and the other retractor is provided on the inferior half.

3. The eyelid speculum of claim 2, wherein the multiple depressions are provided on a medial side of the eyelid speculum and the multiple needle guide recesses are provided on a lateral side of the eyelid speculum, such that, when the eyelid speculum is applied to the patient's eye, the depressions are oriented toward a medial canthus of the patient's eye and the needle guide recesses are oriented toward a lateral canthus of the patient's eye.

4. The eyelid speculum of claim 2 and further comprising grooves in the anterior surface of the ring-shaped body, wherein the grooves connect with the central opening and extend along the axis of symmetry.

5. The eyelid speculum of claim 1, further comprising multiple grooves in the anterior surface of the ring-shaped body connected with the central opening, wherein one groove of the multiple grooves extends between the depressions and another groove the multiple grooves extends between the needle guide recesses.

6. The eyelid speculum of claim 1, wherein the body is formed from titanium, stainless steel, or polymethylmethacrylate.

7. The eyelid speculum of claim 1, wherein the pair of eyelid retractors extend from the anterior surface of the ring-shaped body.

8. The eyelid speculum of claim 7, wherein the pair of eyelid retractors define a pocket which receive portions of the patient's eyelids.

9. The eyelid speculum of claim 1, wherein the pair of eyelid retractors are hooked-shaped, with an elongated support extending from the ring-shaped body and an elongated flange extending from the support.

10. The eyelid speculum of claim 9, wherein the support of each of the pair of eyelid retractors extends transversely across the anterior surface, and projects generally normally from the anterior surface between the inner and outer peripheral surfaces.

11. The eyelid speculum of claim 9, wherein the flange of each of the pair of eyelid retractors extends from the support to a hook end facing toward the outer peripheral surface and which is curved to fit a patient's eyelid.

12. The eyelid speculum of claim 1, wherein the central opening comprises a diameter of approximately 11-12 mm and the posterior surface comprises a radius of curvature of approximately 12 mm.

13. An eyelid speculum for holding eyelids of a patient's eye open during a medical procedure, comprising:
 a ring-shaped body insertable onto the patient's eye and including an inner peripheral surface, an outer peripheral surface, an anterior surface, and a posterior surface;
 a pair of eyelid retractors provided on the ring-shaped body;
 a central opening defined by the inner peripheral surface of the ring-shaped body, between the pair of eyelid retractors, which is sized to permit a view of a cornea of the patient's eye during the medical procedure;
 multiple depressions on the anterior surface of the ring-shaped body, separate from the pair of eyelid retractors; and
 multiple needle guide recesses in the outer peripheral surface of the ring-shaped body;
 wherein, when applied to the patient's eye, the ring-shaped body fits on a conjunctiva and sclera of the patient's eye, with the posterior surface resting on the patient's eye and with the central opening exposing the cornea;
 wherein the eyelid speculum defines an axis of symmetry that divides the eyelid speculum into generally identical superior and inferior halves, wherein one eyelid retractor of the pair of eyelid retractors is provided on the superior half and the other eyelid retractor of the pair of eyelid retractors is provided on the inferior half; and
 wherein the multiple depressions are provided on a medial side of the eyelid speculum and the multiple needle guide recesses are provided on a lateral side of the eyelid speculum, such that, when the eyelid speculum is applied to the patient's eye, the depressions are oriented toward a medial canthus of the patient's eye and the needle guide recesses are oriented toward a lateral canthus of the patient's eye.

14. The eyelid speculum of claim 13, wherein the multiple depressions are cup-shaped, and comprises a bottom wall and a side wall extending from the anterior surface to the bottom wall.

15. The eyelid speculum of claim 13, wherein the multiple needle guide recess comprises an incurved section of the outer peripheral surface.

16. The eyelid speculum of claim 13, and further comprising grooves in the anterior surface of the ring-shaped body, wherein the grooves connect with the central opening.

17. The eyelid speculum of claim 13, formed from titanium, stainless steel, or polymethylmethacrylate.

18. A sterile medical kit including an eyelid speculum according to claim 13, and at least one of a syringe, sterile cotton, antiseptic, or a cotton-tipped applicator.

19. An eyelid speculum for holding eyelids of a patient's eye open during a medical procedure, comprising:
 a ring-shaped body insertable onto the patient's eye and including an inner peripheral surface, an outer peripheral surface, an anterior surface, and a posterior surface;
 a pair of eyelid retractors provided on the ring-shaped body;
 a central opening defined by the inner peripheral surface of the ring-shaped body, between the pair of eyelid retractors, which is sized to permit a view of a cornea of the patient's eye during the medical procedure;
 multiple depressions on the anterior surface of the ring-shaped body, separate from the pair of eyelid retractors;
 multiple needle guide recesses in the outer peripheral surface of the ring-shaped body; and
 multiple grooves in the anterior surface of the ring-shaped body connected with the central opening, wherein one groove of the multiple grooves extends between the depressions and another groove of the multiple grooves extends between the needle guide recesses;
 wherein, when applied to the patient's eye, the ring-shaped body fits on a conjunctiva and sclera of the patient's eye, with the posterior surface resting on the patient's eye and with the central opening exposing the cornea.

20. The eyelid speculum of claim 19, wherein the multiple needle guide recesses comprise an incurved section of the outer peripheral surface.

* * * * *